United States Patent
Aghakhani

(10) Patent No.: US 10,874,706 B2
(45) Date of Patent: Dec. 29, 2020

(54) COMPOSITION FOR IMPROVING LACTATION

(71) Applicant: Ancient Formulas, Inc., Wichita, KS (US)

(72) Inventor: Gohlam Abbas Aghakhani, Wichita, KS (US)

(73) Assignee: Ancient Formulas, Inc., Wichita, KS (US)

( * ) Notice: Subject to any disclaimer, the term of this patent is extended or adjusted under 35 U.S.C. 154(b) by 396 days.

(21) Appl. No.: 15/185,823

(22) Filed: Jun. 17, 2016

(65) Prior Publication Data

US 2016/0296580 A1 Oct. 13, 2016

Related U.S. Application Data

(63) Continuation of application No. 14/561,072, filed on Dec. 4, 2014, now abandoned, which is a continuation of application No. 13/394,538, filed on May 22, 2012, now abandoned.

(51) Int. Cl.

| | |
|---|---|
| *A61K 36/48* | (2006.01) |
| *A61K 31/10* | (2006.01) |
| *A61K 36/03* | (2006.01) |
| *A61K 36/235* | (2006.01) |
| *A61K 36/73* | (2006.01) |
| *A61K 36/889* | (2006.01) |
| *A61K 45/06* | (2006.01) |

(52) U.S. Cl.
CPC .............. *A61K 36/48* (2013.01); *A61K 31/10* (2013.01); *A61K 36/03* (2013.01); *A61K 36/235* (2013.01); *A61K 36/73* (2013.01); *A61K 36/889* (2013.01); *A61K 45/06* (2013.01)

(58) Field of Classification Search
None
See application file for complete search history.

(56) References Cited

U.S. PATENT DOCUMENTS 5,997,877 A * 12/1999 Chang ............... A23J 1/006
424/757
7,544,376 B2 * 6/2009 McNeff .................. A61K 36/00
424/725

OTHER PUBLICATIONS

Abascal et al. (2008) Alternative and Complementary Therapies, vol. 14, No. 6. 288-294 (Year: 2008).*
Zapantis et al. (2012) J. Pharmacy Practice, 25(2): 222-231. (Year: 2012).*
Mohanty et al. (2014) Veterinary World, vol. 7(5): 325-330. (Year: 2014).*

* cited by examiner

*Primary Examiner* — Russell G Fiebig
(74) *Attorney, Agent, or Firm* — Jenei LLC; Stephen Jenei

(57) ABSTRACT

Disclosed is a novel composition effective to improve lactation and milk production in an animal. In some embodiments the composition comprises a fiber-depleted fraction derived from fenugreek in combination with additives that synergistically improve the effective of the composition. Additives that enhance the effect of the fenugreek fraction can include apple cider vinegar, fennel seed powder, saw palmetto berry extract, kelp powder, and methylsulfonylmethane.

5 Claims, 3 Drawing Sheets

COMPOSITION FOR IMPROVING LACTATION

CROSS-REFERENCE TO RELATED APPLICATIONS

This application is a continuation of U.S. application Ser. No. 14/561,072 filed Dec. 4, 2014 and entitled "COMPOSITION FOR IMPROVING LACTATION", which is a continuation of U.S. application Ser. No. 13/394,538 filed May 22, 2012 and entitled "COMPOSITION FOR IMPROVING LACTATION" for all commonly disclosed subject matter, which is expressly incorporated herein by reference in its entirety to form part of the present disclosure for all purposes.

FIELD OF THE INVENTION

The invention is in the field of compositions effective to improve milk output in lactating mammals, in particular feed compositions that comprise a fiber-depleted fenugreek fraction.

BACKGROUND

Fenugreek has attracted considerable interest as a natural source of soluble dietary fiber and diosgenin (sapogenin). The fenugreek seed comprises a central hard, yellow embryo surrounded by a corneous and comparatively large layer of white, semitransparent endosperm. This and the sperm contains galactomannan gum, analysed as soluble dietary fiber. The endosperm is surrounded by a tenacious, dark brown husk.

There are commercial uses for the various fractions of the fenugreek seed. The commercial fenugreek oleoresins are used as an ingredient for imitation maple flavors and is effective in butter, butterscotch, black walnut, nut and spice flavors. Another fraction of the fenugreek seed has been found to comprise a quantity of saponins. Fenugreek seed saponins are steroidal in nature with the diosgenin as the main sapogenin. Fenugreek has also been cited as useful in stimulating milk production in mammals. Improving output from dairy herds in particular has been a long standing interest in farming, and a variety of prior art methods have been used in an attempt to improve milk production efficiency. For example, feeding dairy cows a mixture of gelatinized corn starch, urea, and yeast culture, has been shown to improve milk production efficiency (Cooke et al., J. Dairy Sci. 90: 360-364). Other examples of feed additive methods include those disclosed in U.S. Pat. No. 5,496,571 (Blagdon et al.), U.S. Pat. No. 5,219,596 (Smith et al.) and U.S. Pat. No. 4,388,327 (Cummins). Extracts of natural products have also been used as feed additives, for example yucca extracts. However, in some cases, these extracts have not been effective in increasing milk production when fed as a portion of the daily ration (Wilson et al., 1998, J. Dairy Sci., 81: 1022-1027).

Other methods include the use of hormonal promoters such as synthetic bovine somatotropin (sBST) to improve yields. One significant problem with the use of sBST is that the use of hormonal promoters is currently banned in the European Union and Canada, a major market for milk production and milk products, limiting their utility. In addition, there are health concerns related to the use of hormonal promoters in cows with respect to their potential effects on human health, as well as on animal health as well. For example, the Food and Drug Administration (FDA) requires labeling on the synthetic hormonal feed supplement Posilac to include reference to the disorders associated with the use of hormonal supplements.

SUMMARY OF THE INVENTION

As a result of the problems and limitations of prior art methods and compositions intended to improve dairy production, what is needed in the dairy industry is a natural product that is effective in promoting increased lactation and improved animal health, and which avoids problems associated with the use of synthetic hormonal promoters. The present invention provides a natural source composition that is effective in improving dairy production, and which improves upon prior art compositions.

In some embodiments, the composition comprises a fiber-depleted fraction of fenugreek seed and other additives (FDF). In some embodiments, the composition comprises a fiber-depleted fraction of fenugreek as well as additional additives. In some embodiments the additives comprise fennel seed powder, kelp powder, methysulfonylmethane (MSM), saw palmetto berry powder, and apple cider vinegar powder. The use of FDF provides a synergistic effect over whole fenugreek seed by removing various non-nutritive fiber fractions that appear to limit the efficacy of fenugreek as a lactation inducer.

In some embodiments the invention comprises a pharmacologically active composition derived from fenugreek, and effective to improve lactation in a vertebrate, the composition comprising: a fiber-depleted fenugreek fraction; and at least one additive, wherein the at least one additive acts synergistically with the fiber-depleted fenugreek fraction to improve lactation.

In some embodiments, the fiber-depleted fenugreek fraction comprises at about 70-75% (w/w) of the composition.

In some embodiments the at least one additive comprises at least one of fennel seed powder, apple cider vinegar, Saw Palmetto berry extract, kelp powder, and methylsulfonylmethane. In some embodiments the at least one additive comprises: about 1-4% (w/w) apple cider vinegar; about 10-14% (w/w) fennel seed powder; about 1-4% Saw Palmetto berry extract; about 1-4% (w/w) kelp powder; and about 3-7% methylsulfonylmethane (w/w).

In some embodiments the composition is pre-packaged in a single ration form. In some embodiments the single ration form comprises from about 0.1 lb to about 0.2 lb of the composition. In some embodiments the composition if effective to improve lactation in the animal, without causing a significant increase in somatic cell counts, as compared to somatic cell counts in an animal not fed the composition. In some embodiments the composition is effective to improve lactation in the animal, without causing a substantial change in milk composition, as compared to milk composition in an animal not fed the composition.

The compositions of the present invention are effective to improve dairy production, even in chronically under-producing animals. The compositions provide the additional advantage in that they are natural products and thus are safe to use both respect to the animals being fed, and the downstream consumer of the dairy products produced. A further advantage is provided in that the products are economical to use and improve the income:feed ratio relative to animals not receiving the supplement.

These and other features are explained more fully in the embodiments illustrated below. It should be understood that in general the features of one embodiment also may be used in combination with features of another embodiment and that the embodiments are not intended to limit the scope of the invention.

BRIEF DESCRIPTION OF THE DRAWINGS

The various exemplary embodiments of the present invention, which will become more apparent as the description proceeds, are described in the following detailed description in conjunction with the accompanying drawings, in which.

DETAILED DESCRIPTION

Figure 1:
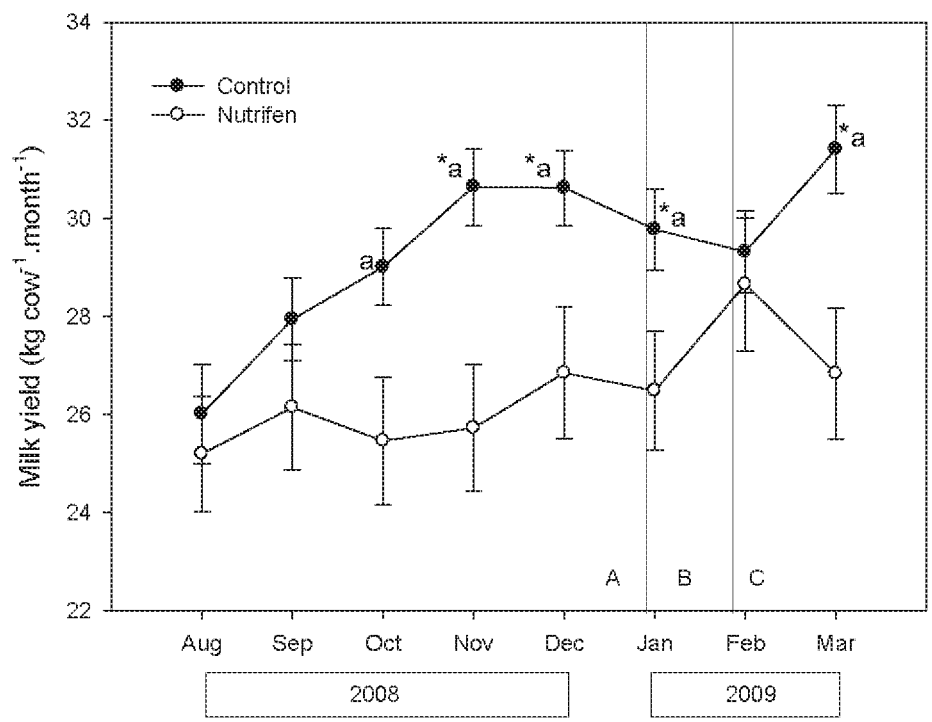
FIG. 1. Milk yield from lactating dairy cows fed a control (n=111) diet or a diet containing FDF (n=50). Cows allocated to the FDF group received the test supplement from Jan. 27, 2009 through Feb. 23, 2009 inclusive. Control cows received their normal basal diet during this time. 'A' denotes pre-supplementation; 'B' denotes supplementation; 'C' denotes post-supplementation. * denotes significant changes from August 2008 within treatment groups; letters denote significant differences between treatment groups within a given month.

Fenugreek (*Trigonella foenum-graecum*) has been a component of human and animal diets for centuries. The benefits of this herb are numerous and a number of health related claims have been made with respect to this herb including use as a treatment for bronchitis, fevers, digestive ailments, rheumatic pain, and boils.

Fenugreek also has a long history of use as a galactagogue in many human cultures (Gabay, 2002; Titan, 2003). This herb has also been fed to animals, and Vermont folk medicine literature describes using fenugreek as fodder to increase milk production. Despite this, little is known about the underlying mechanisms of action, or whether there are sub-fractions of fenugreek that would be more effective in stimulating lactation if separated from other components of the plant. As a result, its historical use, together with its high feeding value (Mir et al., 1997; 1998) provided the rationale for investigating its potential to improve milk production in lactating livestock.

In the present invention, a FDF is used as a supplement to the normal daily food ration provided to a lactating mammal. It has been found that an extract of fenugreek from which fiber has been removed is more effective as a galactagogue than is unprocessed fenugreek. Thus, what has been observed is an unexpected superior result which appears to occur when dietary fiber and associated components are removed from whole fenugreek.

FDF is a novel dairy cow supplement based upon fenugreek. FDF is produced from the cotyledon fraction of the fenugreek seed. In one embodiment, the FDF comprises a fiber-depleted fraction produced according to methods described in U.S. Pat. No. 5,997,877 (Chang). A comparative analysis of FDF and whole seed is provided in Table 1.

FDF has a lower fiber content than whole fenugreek seed, owing primarily to a decrease in soluble dietary fiber, and higher protein content than whole fenugreek seed. In some embodiments, FDF comprises galactomannan-depleted fenugreek seed powder meal (about 70-75% w/w), with the remainder of the composition comprising apple cider vinegar (about 1-4% w/w), Serenoa repens (Saw Palmetto) berry extract (about 1-4% w/w) and *Foeniculum vulgare* (Fennel) seed extract (about 10-14% w/w), kelp powder (about 1-4% w/w) and methyl sulfonyl methane (MSM) (about 3-7% w/w).

In one embodiment, the composition of FDF comprised 73.2% fiber-depleted fenugreek seed powder, 12.2% fennel seed powder, 4.9% kelp powder. 4.9% MSM, 2.4% Saw palmetto berry powder, and 2.4% apple cider vinegar powder. All amounts are on a w/w basis.

In some embodiments, the amount of fiber-depleted fenugreek seed powder comprises from about 70-80% (w/w) of the FDF, with the remaining 20-30% (w/w) comprising other additives, for example, and without being limiting fennel seed powder, kelp powder, MSM, Saw palmetto berry powder, and apple cider vinegar powder. Other common feed additives can be included in the FDF without reducing the efficacy of the fiber-depleted fenugreek fraction.

In some embodiments, FDF can be provided to dairy animals at a rate of about 0.1 to about 0.2 lb. per feeding per animal. In some embodiments, FDF is provided at about 0.12 to about 0.15 lb. per feeding per animal. Typically, animals are fed twice per day, so that the total amount of FDF provided may range from about 0.2 to about 0.4 lb. per day per animal.

The FDF can be fed as a part of each food ration or on an intermittent basis. For example, a method of feeding could comprise including FDF with the normal feed ration for a period of 4 weeks, followed by a period where no supplement was provided. Alternatively, it may be desirable to maintain animals on a diet that includes the FDF for extended periods of time, up to the time during which the animal is in use for milk production.

FDF can be fed to animals that have been identified as under-producing, as well as to those that have been observed to have milk outputs within normal ranges. Providing the supplement is expected to increase milk production compared to that which would be achieved in the absence of supplement.

The following example is an embodiment of a method of feeding dairy cows with FDF, and the results that can be expected. The example is but one possible method of feeding, and is not intended to be limiting to the scope of the invention. Those skilled in the art will recognize that variations may be made in the composition of the FDF without departing from the scope of the invention.

Example 1

A field study was carried out on two dairy farms to determine the effect of a novel dietary supplement based upon a fiber-depleted fenugreek (FDF) on milk production by lactating dairy cows. Fifty lactating holstein cows in Dairy #1 with milk production below the herd average for at least 4 consecutive months were fed FDF (0.136 lb. b.i.d.) for 27 days. Milk yield, somatic cell count, milk protein, milk fat and income:feed ratios were compared with 111 high-producing control cows. In a second experiment, 150 lactating Holstein cows in Dairy #2 were all provided with FDF (0.136 lb. b. i. d.) for 39 days. Milk yield was compared with that of 5 months prior to supplementation, as well as with production records for the same cows 12 months earlier.

Results from Dairy #1 indicate that the chronically low-producing cows fed FDF increased their productivity such that they were not significantly different from high-producing control cows. There was no significant effect of FDF on milk composition or somatic cell count, but there was an improvement in Income:Feed compared with high-producing controls. Cows in Dairy #2 increased their milk production 24% over predicted yields after treatment with FDF. Results support a use for FDF in improving milk production in both low- and high-producing dairy cattle. Future studies should investigate dose optimization and a longer supplementation period to determine how best to incorporate the supplement into commercial dairy production.

Methods

The experiments were performed on two farms, Dairy #1 and Dairy #2 respectively, located in the same area. A total of 161 mature, lactating Holstein cows were recruited from Dairy #1 and a total of 150 mature, lactating Holstein cows were recruited from Dairy #2.

Dairy #1

Milk Yield (MKY; lb./cow/month) and Somatic Cell Count (SCC; $\times 10^3$ cells/mL milk/cow/month) were recorded monthly from Aug. 27, 2008 through Mar. 25, 2009. Days in Lactation, Milk Fat (MF; %), Milk Protein (MP; %) in January (pre-supplementation), February (supplementation) and March (post-supplementation) were also recorded.

Cows were non-randomly assigned to either control (did not receive FDF) (n=111) or FDF groups (n=50). In this particular example, the FDF group included only cows with MKY chronically below the herd average. However, the invention is non-limiting in this respect and FDF can be provided to animals previously identified as having below average, average, or above average milk production when fed a non-supplemented diet. Criteria for allocation to FDF group included an MKY<60 lb. per month and SCC values >245.times.10.sup.3 cells/mL of milk during the 5 consecutive months preceding the supplementation period (the "collection period"). Cows allocated to the FDF group received the test supplement as part of their normal ration from Jan. 27, 2009 through Feb. 23, 2009 inclusive (the "supplementation period"). Control cows received their normal basal diet during this time. All cows received 75 lb. daily of a Total Mixed lactating dairy ration (TMR) which met their nutritional requirements (Table 2a and 2b) twice daily. In addition to the TMR, cows in the FDF group received 0.136 lb. of the FDF at each feeding.

Dairy #2

Total Milk (TM; lb.) produced by 150 dairy cows was collected from the milk tank was recorded every 2 days, for a period of 204 days. Twice daily, all cows received the Total Mixed lactating dairy ration (TMR) which met their nutritional requirements (Table 3a and 3b). All cows (n=150) received the FDF (0.371 lb. per day) for a period of 42 days. Cows in the treatment group received FDF in addition to their basal diet between days 0 and 56. Control cows received their basal diet throughout the supplementation period. In order to compare performance from the same sampling interval from the previous year, TM data from the current year and the previous year were also compared.

Data Analysis

All data are expressed as mean±SEM.

Dairy #1: Two-way Repeated Measures Analysis of Variance (RM-ANOVA) was conducted in order to detect interactions between time and treatment. Individual 1-way RM-ANOVA was conducted on data from control and FDF groups to detect significant effect of time within each group. Differences between groups at individual time points were analyzed using a 1-way ANOVA without RM. When a significant F-ratio was obtained, the Holm-Sidak post-hoc method was used to identify significantly different means. Significance was accepted when P<0.05 at a minimum statistical power of 0.8.

Dairy #2: Individual One-way ANOVA wer milk composition e used to detect significant effect of time on MKY during the collection period and supplementation period. A 2.sup.nd order polynomial regression equation was derived from average MKY per month for all cows during the collection period. This equation was used to calculate predicted Milk Yield (PMY) for the supplementation period assuming no intervention with FDF. MKY was divided by PMY and then multiplied by 100 in order to determine % of PMY. MKY from the current year and the previous year was compared with MY January through March 2009 using a 2-way ANOVA; the Holm-Sidak post-hoc method was used to identify significantly different means. Significance was accepted when P<0.05 at a minimum statistical power of 0.8.

Results

Dairy #1

Milk Yield

There was considerable variability in MKY in the FDF group during the collection period, and no significant changes over time were observed. In the control group there was a consistent increase in milk yield for the first three months of the collection period, which declined over the month preceding the supplementation period. Increases in MKY in control cows over baseline (August 2008) were significant in November and December 2008, and January and March 2009 (FIG. 1).

During the collection period MKY was significantly higher in the control group than the FDF group in October (P=0.01), November (P=0.002), December (P=0.012), January (P=0.034) and March (P=0.004). There was no significant difference in MKY between groups in February (p=0.694) (FIG. 1).

Figure 2:
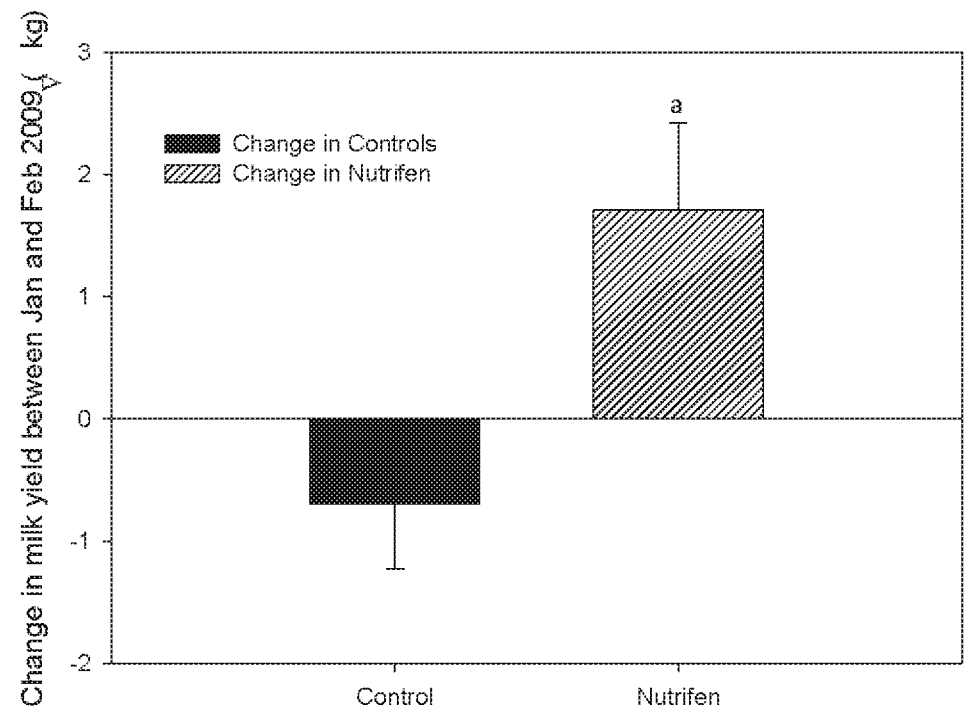
FIG. 2. Change in Milk Yield from January to February 2009 (after supplementation with FDF). Cows allocated to the FDF group received the test supplement from Jan. 27, 2009 through Feb. 23, 2009 inclusive. Control cows received their normal basal diet during this time. Letters denote significant differences between treatment groups.

The change in MKY between January and February 2009 was significantly different between control and FDF groups (P=0.012) (FIG. 2).

Somatic Cell Count Score (SCCS)

Figure 3:
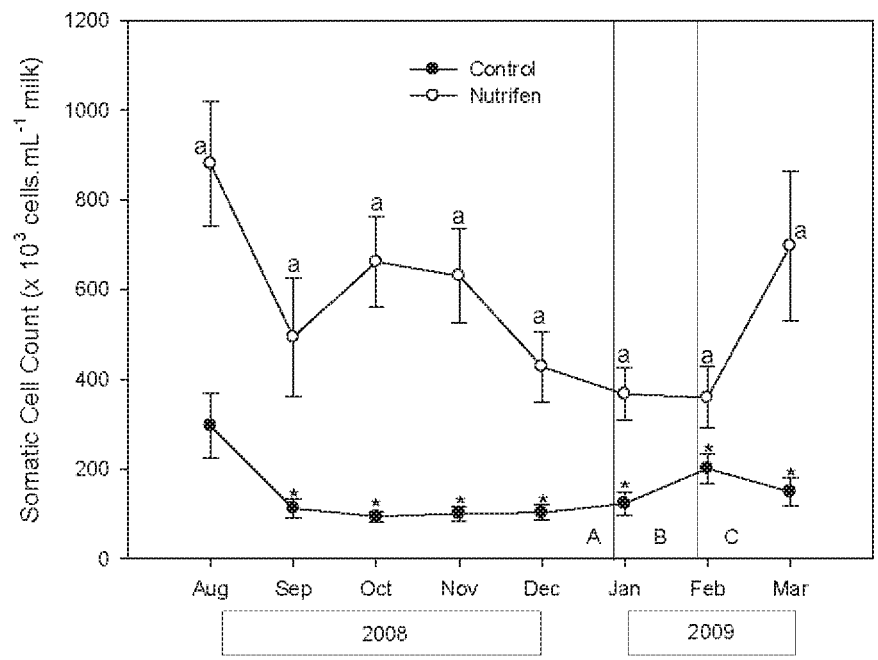
FIG. 3. Somatic Cell Count from lactating dairy cows fed a control (n=111) diet or a diet containing FDF (n=50). Cows allocated to the FDF group received the test supplement from Jan. 27, 2009 through Feb. 23, 2009 inclusive. Control cows received their normal basal diet during this time. 'A' denotes pre-supplementation; 'B' denotes supplementation; 'C' denotes post-supplementation. * denotes significant changes from August 2008 within treatment groups; letters denote significant differences between treatment groups within a given month.

In control cows, SCCS was significantly higher in August 2008 than in all subsequent months (FIG. 3). SCCS was significantly lower in control cows than in treatment cows at all time points. There were no significant changes in SCCS in treatment cows over the study duration.

Days in Lactation

Mean Days in Lactation in January 2009 (before beginning supplementation) for control (186.8±10.7 days) and treatment groups (162.9±20.7 days) were not significantly different.

Milk Composition

There were no significant changes in % fat in milk in treatment or control cows (Table 3). Percent protein was also unchanged in control cows, but in cows provided FDF % protein was significantly lower in March than in January.

Income:Feed Ratio

There was a significant decline in the Income:Feed ratio in control cows at each interval between January and March 2009 (Table 4). There was also a significant decline in Income:Feed ratio in March in FDF cows, but not during February (during supplementation with FDF). The Income:Feed ratio was significantly lower in FDF cows than in controls (as expected given their selection based upon sub-standard productivity). However, unlike control cows, there was no significant decline in the Income:Feed ratio between January and February (after supplementation with FDF). In the month following termination of FDF supplementation, the Income:Feed ratio decreased significantly in treatment cows.

Dairy #2

Figure 4:
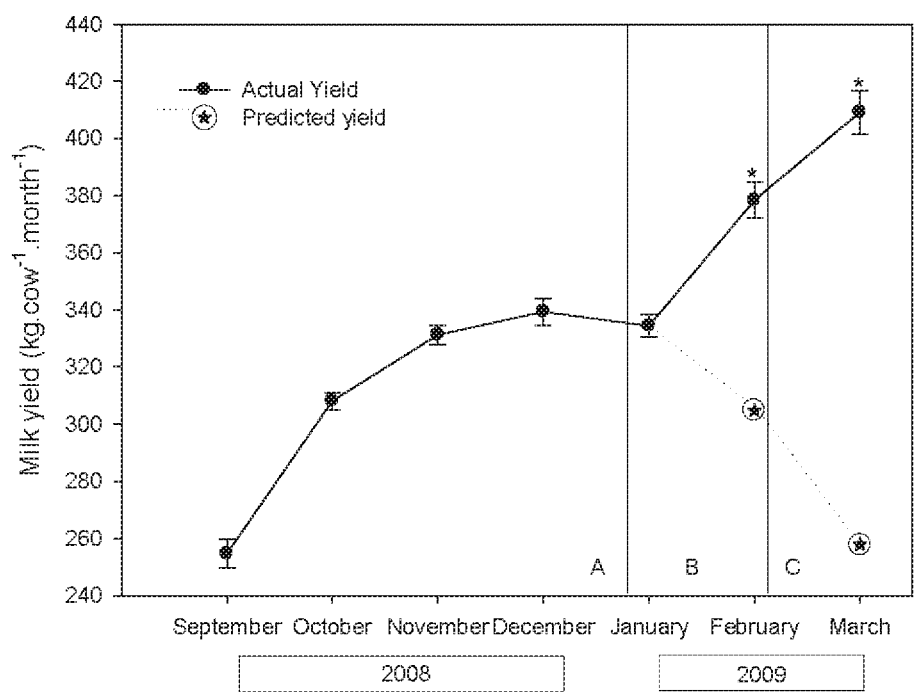
FIG. 4. Actual vs Predicted Milk Yield in Dairy Cows Supplemented with FDF (0.371 lbs/day). All cows (n=150) received the FDF supplement (0.371 lbs/day) from Jan. 23, 2009 through Mar. 3, 2009. Predicted Milk Yield was calculated from regression analysis of actual milk yield from Sep. 1 through Jan. 21, 2009. 'N denotes pre-supplementation; 'B' denotes supplementation; 'C' denotes post-supplementation. * denotes significant increase from January 2009 (i.e., pre-supplementation).

Across the period of September 2008 through March 2009, MKY during February and March 2009 was significantly higher than every preceding month, coinciding with supplementation with FDF (FIG. 4). Predicted MKY (per cow/month) for February and March 2009 was 677.2 and 573.1 lb. (respectively) compared with actual MKY for February and March of 840.9±17.43 lb. and 909.2±16.6 lb. (respectively) (FIG. 4). This represents increases of 24.16% and 58.7% respectively over the predicted MKY values.

Comparison of Performance January-March 2008 vs January-March 2009

Figure 5:
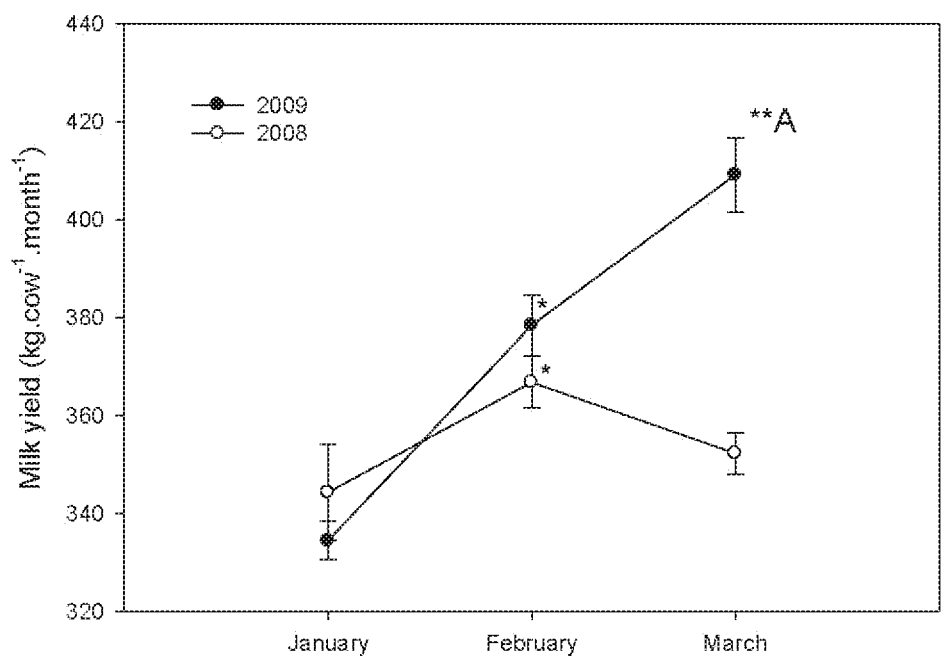
FIG. 5. Comparison of monthly MKY in January, February, March in 2008 and 2009. All cows (n=150) received the FDF supplement (0.371 lbs/day) from Jan. 23, 2009 through Mar. 3, 2009. No supplement was fed in 2008. * denotes significant (p<0.05) increase from January value of the same year. Letters denote significant difference (P<0.001) between years during that month.
Figure 6:
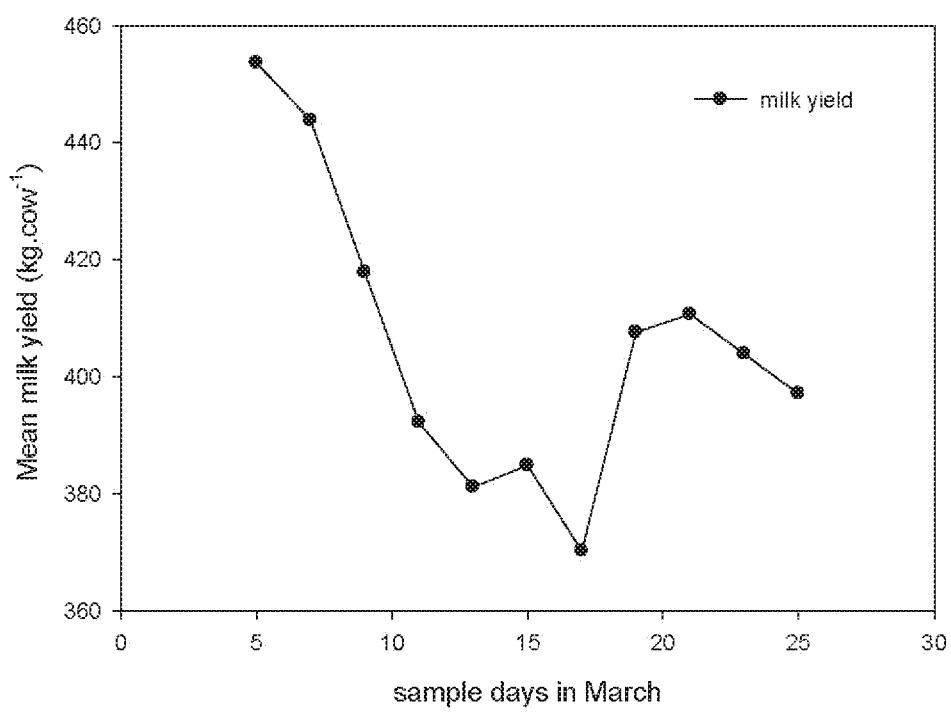
FIG. 6. Milk yield (lb/cow) on each day of March. All cows (n=150) received the FDF supplement (0.371 lbs/day) from Jan. 23, 2009 through Mar. 3, 2009. Data presented are data collection days after removal of FDF.

MKY increased significantly between January and February in both 2008 and 2009 (FIG. 5). MKY was still significantly increased in March 2009 (909.2±16.6 lb.) compared with January 2009 (743.1±8.7 lb.), whereas there was no further increase in March 2008 (782.8±9.4 lb.) compared with January 2008 (765.0±21.8 lb.). MKY in February 2009 was non-significantly (P<0.1) higher than in February 2008, and significantly higher in March 2009 compared with March 2008 (P<0.001). Elevated milk production in March was primarily due to substantially elevated milk production at the beginning of month while FDF was still being fed. Milk production fell rapidly after removal of the supplement and returned to pre-supplementation levels with one week (FIG. 6).

Discussion

This is the first study to report the effect of a fenugreek meal-based supplement in a commercial dairy cow operation typical of North American dairy production. The data provide evidence that the product effectively increases milk yield in both high- and low-producing dairy cattle and may improve Income:Feed in those cattle with chronically low milk production. In particular, FDF appears to be more effective than would be an equivalent amount of unprocessed fenugreek, suggesting that superior results are obtained by using the fiber-depleted product.

Cows at Dairy #1 were selected for the treatment group based on chronically low milk production. Analysis of their production records revealed that these cows also had substantially elevated SCCs compared with the control group, and contributed significantly less to dairy profit than the control group as evidenced by lower Income:Feed ratios. The difference in milk yield between treatment and control groups was significant every month between October 2008 and March 2009 except during the month of supplementation with FDF. At this point, milk yield in the chronic low producers was not significantly different from the herd average. Milk yield declined in the treatment group immediately after removal of supplementation despite the fact that milk yield actually increased in controls. Thus, there does not appear to be any residual benefit of feeding FDF after termination of supplementation. Importantly, profitability of these low-producing cows appeared to be improved subsequent to supplementation with FDF despite the additional cost of producing the TMR.

Similar results were obtained when cows at Dairy #2 were provided with dietary FDF. While no control group was maintained at this Dairy, regression analysis of the previous 5 months of production records provides evidence that milk production was significantly increased after the cows were fed FDF, and the improvement in milk production rapidly declined after removal of the supplement.

These data are consistent with previous reports of improved milk yield in livestock fed whole fenugreek. Alamar and Basiouni (2005) reported a 13% increase in milk yield in 6 lactating dairy goats fed fenugreek seeds (60 g/day) for 60 days compared with 6 control goats. A 13% increase in milk production was also reported for 6 lactating buffalo provided with a dietary supplement containing fenugreek (200 g) once every 4 days for a total of 60 days, as compared with 6 controls (Tomar et al. 1996). The supplement in this study also contained linseed oil and cane sugar; 6 buffalo treated with just the cane sugar and linseed oil had significantly reduced milk production compared to controls, supporting an essential role of fenugreek in the observed increase in milk production. Other authors report no significant effect of dietary fenugreek (20% DMI) for 3 weeks on milk production in lactating dairy cows, though blood and milk cholesterol levels were significantly reduced (Shah and Mir, 2004). This study was shorter term than the current study and also recruited on three animals per group and thus was likely underpowered for detection of differences in milk yield.

Increases in milk yield were markedly higher in the current study than in the aforementioned studies. This suggests that the fiber-depleted fenugreek is more effective at improving milk production than is fenugreek alone. In addition, is anticipated that the other constituents of FDF act synergistically with components from fenugreek to contribute to the observed effect. Saw palmetto (Serenoa repens) has widely reported anti-androgenic effects (Ulbricht et al., 2006) including possible anti-estrogenic activity (Di Silverio et al., 1992), though its effect on milk production has not been investigated. Similarly, fennel (*Foeniculum vulgare*) is a putative estrogenic agent (Albert-Puleo, 1980). Trans-anethole, a phytochemical found in fennel (Gosge et al., 2008), has demonstrated estrogenic activity in vitro (Howes et al., 2002; Nakagawa and Suzuki, 2003) though, like Saw palmetto, there are no reports of its effect on milk production. MSM is provided in FDF as a source of sulphur, an important macromineral in human breast milk (Parcell, 2002).

The mechanism of galactagogue action of FDF is not fully known, and so the applicants, while speculating on how fenugreek acts to improve milk production, are not bound to any one particular theory of operation. Since there was no change in SCCs in Dairy #1 it is unlikely that the supplement produced an immune-mediated or anti-inflammatory effect. Examination of other reported biological effects of dietary fenugreek point to a hormone related mechanism—specifically, a stimulatory effect of fenugreek on plasma ghrelin. Exogenous ghrelin provided to lactating dairy cows has resulted in increased milk yield (Roche et al., 2008b), and endogenous ghrelin is increased during lactation, probably as physiological means for increasing feed intake and maintaining energy balance (Abizaid et al., 2008; Roche et al., 2008a). Ghrelin plays a key role in regulating feed intake, with elevated plasma ghrelin associated with increased feed intake (Roche et al., 2008).

Fenugreek has also been associated with increased feed intake (Petit et al., 1993; Rguibi and Belahsen, 2006). Increases in plasma ghrelin is also causative of elevated plasma growth hormone (Nass et al., 2008), an effect reported subsequent to fenugreek feeding (Shim et al., 2008; Alamar and Basiouni, 2005). Interestingly, polymorphisms in the ghrelin gene are associated with feed efficiency in beef cattle (Sherman et al., 2008); beef cattle provided with a diet rich in fenugreek have shown significantly improved feed efficiency (Okine et al., 2001).

Connections with ghrelin also exist within the effects of fenugreek on glucose metabolism. The seed is well established as a tool to control diabetes, primarily due to its ability to increase insulin sensitivity of adipose tissue, skeletal muscle and liver (Hannan et al., 2007; Gad et al., 2006), and lower serum levels of low density lipoproteins (LDL) (Hannan et al., 2003; Sowmya and Rajyalakshmi 1999). Insulin sensitivity and glucose metabolism are involved in the complex endocrine regulation of feeding behaviour. Among the most important predictors for elevated serum ghrelin is insulin sensitivity (Kempa et al., 2007). Dietary compounds which increase insulin sensitivity, such as fenugreek (Gupta et al., 2001), would thus be predicted to increase serum concentrations of ghrelin.

The biological activity of ghrelin in serum is dependent on its octanoylation status, such that octanoylated form of ghrelin participates primarily in increasing appetite (De Vriese et al., 2007), while the degradation form of ghrelin (desacyl ghrelin) has other effects, including inhibition of feed intake (Asakawa et al., 2005). Enzymes responsible for degradation of ghrelin to desacyl ghrelin are those associated with lipoproteins, and mainly with LDL (De Vriese et al., 2007). Thus, dietary products that are able to influence the profile of serum lipoproteins in favour of high density lipoprotein (HDL) and reducing LDL, such as fenugreek, will limit interactions of enzymes associated with LDL with ghrelin, thus reducing ghrelin degradation and sustaining appetite.

In summary the current study provides evidence that a fenugreek-based dietary supplement (FDF) significantly improves milk yield in low- and high-producing dairy cows without changing milk composition or somatic cell count score. Further, the effect appears superior to those that would be obtained using unprocessed fenugreek, indicating that the use of a fiber-depleted fenugreek extract is an effective way in which to improve milk production in mammals, and in particular in dairy cows.

Tables

TABLE 1

Comparative composition of FDF and fenugreek whole seed.

| Proximate analysis | Fenugreek whole seed | FDF |
|---|---|---|
| Moisture | 13.1 | 14.1 |
| Total Dietary Fiber | 44.5 | 26.9 |
| Soluble Dietary Fiber | 17.6 | 5.29 |
| Insoluble Dietary Fiber | 26.9 | 21.7 |
| Protein | 28.1 | 38.0 |
| Ash | 3.41 | 4.05 |
| Fat | 7.22 | 12.2 |

TABLE 2a

Feed composition of TMR (Dairy #1)

| Feed # | Feed Ingredient | % DM intake |
|---|---|---|
| 4 | High moisture corn (78.07DM) | 18.46 |
| 30 | Grass hay | 13.14 |
| 44 | Milo silage | 9.25 |
| 46 | Corn silage | 32.46 |
| 66 | Corn - distillers grains | 10.64 |
| 81 | Soybean meal | 12.91 |
| 142 | Plain salt | 0.30 |
| 530 | Basemix | 2.85 |

Table 2b

Nutrient analysis of dairy ration (Dairy #1) (DM Basis)

TABLE 2b

Nutrient analysis of dairy ration (Dairy #1) (DM Basis)

| | Lbs | % |
|---|---|---|
| As fed | 74.38 | — |
| DM | 42.29 | 100 |
| Crude protein | 6.821 | 16.129 |

| X | | Mcal/Lb |
|---|---|---|
| Net Energy (NE) Maint | | 82.933 |
| NE Gain | | 51.084 |
| Ne Lactation | | 76.863 |

| | % |
|---|---|
| Total Digestible Nutrients (TDN) | 74.141 |
| NPN | 0.000 |
| Crude Fat | 4.090 |
| Crude Fibre | 15.337 |
| Acid Detergent Fibre (ADF) | 18.303 |
| Neutral Detergent Fibre (NDF) | 32.554 |
| Ash | 7.890 |
| Calcium | 0.923 |
| Phosphorus | 0.376 |
| Potassium | 1.026 |
| Magnesium | 0.232 |
| Sodium | 0.246 |

TABLE 2b-continued

Nutrient analysis of dairy ration (Dairy #1) (DM Basis)

| | |
|---|---|
| Chloride | 0.339 |
| Salt | 0.296 |
| Sulfur | 0.214 |
| Lysine | 0.831 |
| Methionine | 0.398 |
| Starch | 28.752 |
| DIP | 61.532 |
| UIP | 38.468 |
| NFC | 39.778 |
| Forage NDF | 25.211 |
| Soluble protein | 23.352 | ppm

| | |
|---|---|
| Zinc | 106.773 |
| Iron | 150.112 |
| Copper | 23.710 |
| Manganese | 61.586 |
| Cobalt | 1.202 |
| Iodine | 0.821 |
| Selenium | 0.310 |
| Niacin | 14.591 |
| Thiamine | 1.477 |

IU/lb

| | |
|---|---|
| Vitamin A | 3659.866 |
| Vitamin D3 | 526.056 |
| Vitamin E | 16.117 | meQ/lb

| | |
|---|---|
| Cation-Anion | 14.022 |

REFERENCES

Abizaid A, Schiavo L, Diano S. Hypothalamic and pituitary expression of ghrelin receptor message is increased during lactation. Neurosci Lett. 2008 Aug. 8; 440 (3):206-10.

Albert-Puleo M. Fennel and anise as estrogenic agents. 3 Ethnopharmacol. 1980 December; 2 (4):337-44.

Asakawa, A. Inui, A. Fujimiya, M. Sakamaki R, Shinfuku N, Ueta Y, Meguid M M, Kasuga M. 2007. Stomach regulates energy balance via acylated ghrelin and desacyl ghrelin. Gut 54 (1):18-24.

Cosge B, Kiralan M, Gurbuz B. Characteristics of fatty acids and essential oil from sweet fennel (*Foeniculum vulgare* Mill. var. *dulce*) and bitter fennel fruits (*F. vulgare* Mill. var. *vulgare*) growing in Turkey. Nat Prod Res. 2008; 22 (12):1011-6.

De Vriese C, Hacquebard M, Gregoire F, Carpentier Y, Delporte C. 2007. Ghrelin interacts with human plasma lipoproteins. Endocrinology 148 (5):2355-62.

Di Silverio F, D'Eramo G, Lubrano C, Flammia G P, Sciarra A, Palma E, Caponera M, Sciarra F. Evidence that Serenoa repens extract displays an antiestrogenic activity in prostatic tissue of benign prostatic hypertrophy patients. Eur Urol. 1992; 21 (4):309-14.

Gabay M P. Galactogogues: medications that induce lactation. J Hum Lact. 2002 August; 18 (3):274-9.

Gad M Z, El-Sawalhi M M, Ismail M F, El-Tanbouly N D. Biochemical study of the anti-diabetic action of the Egyptian plants fenugreek and balanites. Mol Cell Biochem. 2006 January; 281 (1-2):173-83.

Gupta A, Gupta R, Lal B. Effect of *Trigonella foenum-graecum* (fenugreek) seeds on glycaemic control and insulin resistance in type 2 diabetes mellitus: a double blind placebo controlled study. J Assoc Physicians India. 2001 November; 49:1057-61.

Hannan J M, Ali L, Rokeya B, Khaleque J, Akhter M, Flatt P R, Abdel-Wahab Y H. Soluble dietary fibre fraction of *Trigonella foenum-graecum* (fenugreek) seed improves glucose homeostasis in animal models of type 1 and type 2 diabetes by delaying carbohydrate digestion and absorption, and enhancing insulin action. Br J Nutr. 2007 March; 97 (3):514-21.

Hannan J M, Rokeya B, Faruque O, Nahar N, Mosihuzzaman M, Azad Khan A K, Ali L. Effect of soluble dietary fibre fraction of *Trigonella foenum graecum* on glycemic, insulinemic, lipidemic and platelet aggregation status of Type 2 diabetic model rats. J Ethnopharmacol. 2003 September; 88 (1):73-7.

Kempa A, Krzyzanowska-Swiniarska B, Miazgowski T, Pilarska K. (2007) Not insulin but insulin sensitivity, leptin, and cortisol are major factors regulating serum acylated ghrelin level in healthy women. J Endocrinol Invest; 30 (8):659-65.

Mir, Z.; Acharya, S. N.; Mir, P. S.; Taylor, W. G.; Zaman, M. S.; Mears, G. J.; Goonewardene, L. A. 1997. Nutrient composition, in vitro gas production and digestibility of fenugreek (*Trigonella foenum-graecum*) and alfalfa forages. Can J Anim Sci 77 (1):119-124.

Mir, Z.; Mir, P. S.; Acharya, S. N.; Zaman, M. S. Taylor, W. G.; Mears, G. J.; McAllister, T. A.; Goonewardene, L. A. 1998. Comparison of alfalfa and fenugreek (*Trigonella foenum-graecum*) silages supplemented with grain on performance of growing steers. Can J Anim Sci 78 (3):343-349.

Nakagawa Y, Suzuki T. Cytotoxic and xenoestrogenic effects via biotransformation of transanethole on isolated rat hepatocytes and cultured MCF-7 human breast cancer cells. Biochem Pharmacol. 2003 Jul. 1; 66 (1):63-73.

Okine E K, Wang Z, Goonewardene Z, Mir Z, Liu M F. Residual metabolizable feed consumption as a method of comparing feed efficiency in steers fed silage and silage-grain diets. Anim Feed Sci Technol. 2001; 92:87-93.

Parcell S. Sulfur in human nutrition and applications in medicine. Altern Med Rev. 2002 February; 7 (1):22-44.

Petit P, Sauvaire Y, Ponsin G, Manteghetti M, Fave A, Ribes G. Effects of a fenugreek seed extract on feeding behaviour in the rat: metabolic-endocrine correlates. Pharmacol Biochem Behav. 1993 June; 45 (2):369-74.

Rguibi M, Belahsen R. Fattening practices among Moroccan Saharawi women. East Mediterr Health J. 2006 September; 12 (5):619-24.

Roche J R, Blache D, Kay J K, Miller D R, Sheahan A J, Miller D W. Neuroendocrine and physiological regulation of intake with particular reference to domesticated ruminant animals. Nutr Res Rev. 2008a December; 21 (2): 207-34.

Roche J R, Sheahan A J, Chagas L M, Blache D, Berry D P, Kay J K. Long-term infusions of ghrelin and obestatin in early lactation dairy cows. J Dairy Sci. 2008b December; 91 (12):4728-40.

Sherman E L, Nkrumah J D, Murdoch B M, Li C, Wang Z, Fu A, Moore S S. Polymorphisms and haplotypes in the bovine neuropeptide Y, growth hormone receptor, ghrelin, insulin-like growth factor 2, and uncoupling proteins 2 and 3 genes and their associations with measures of growth, performance, feed efficiency, and carcass merit in beef cattle. J Anim Sci. 2008 January; 86 (1):1-16.

Shim S H, Lee E J, Kim J S, Kang S S, Ha H, Lee H Y, Kim C, Lee J H, Son K H. Rat growth-hormone release stimulators from fenugreek seeds. Chem Biodivers. 2008 September; 5 (9):1753-61.

Sowmya P, Rajyalakshmi P. Hypocholesterolemic effect of germinated fenugreek seeds in human subjects. Plant Foods Hum Nutr. 1999; 53 (4):359-65.

Tiran D. The use of fenugreek for breast feeding women. Complement Ther Nurs Midwifery. 2003 August; 9 (3): 155-6.

Tomar K S, Singh V P, Yadav R S. 1996. Effect of feeding maithy (*Trigonella foenum-graecum*) and chandrasoor (*Lepidium sativum* L.) seeds on milk and blood constituents of Murrah buffaloes. Ind J An Sci, 66 (11): 1192-1193.

Ulbricht C, Basch E, Bent S, Boon H, Corrado M, Foppa I, Hashmi S, Hammerness P, Kingsbury E, Smith M, Szapary P, Vora M, Weissner W. Evidence-based systematic review of saw palmetto by the Natural Standard Research Collaboration. J Soc Integr Oncol. 2006 Fall; 4 (4):170-86.

Xue W L, Li X S, Zhang J, Liu Y H, Wang Z L, Zhang R J. Effect of *Trigonella foenum-graecum* (fenugreek) extract on blood glucose, blood lipid and hemorheological properties in streptozotocin-induced diabetic rats. Asia Pac J Clin Nutr. 2007; 16 Suppl 1:422-6.

The method may be embodied in an automated manufacturing system that performs a series of functional processes. In some implementations, certain steps of the methods are combined, performed simultaneously or in a different order, or perhaps omitted, without deviating from the scope of the disclosure. Thus, while the method blocks are described and illustrated in a particular sequence, use of a specific sequence of functional processes represented by the blocks is not meant to imply any limitations on the disclosure. Changes may be made with regards to the sequence of processes without departing from the scope of the present disclosure. Use of a particular sequence is therefore, not to be taken in a limiting sense, and the scope of the present disclosure is defined only by the appended claims.

It must be noted that, as used in this specification and the appended claims, the singular forms "a," "an" and "the" include plural referents unless the content clearly dictates otherwise. Thus, for example, reference to a "colorant agent" includes two or more such agents.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

The entire disclosures of all applications, patents and publications cited herein, if any, are herein incorporated by reference. Reference to any prior art in this specification is not, and should not be taken as an acknowledgement or any form of suggestion that that prior art forms part of the common general knowledge in the field of endeavor in any country in the world.

The invention may also be said broadly to consist in the parts, elements and features referred to or indicated in the specification of the application, individually or collectively, in any or all combinations of two or more of the parts, elements or features.

Where in the foregoing description reference has been made to integers or components having known equivalents thereof, those integers are herein incorporated as if individually set forth.

As will be appreciated by one having ordinary skill in the art, the methods and compositions of the invention substantially reduce or eliminate the disadvantages and drawbacks associated with prior art methods and compositions.

It should be noted that, when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

While it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments, which come within the spirit and scope of the present invention.

What is claimed is:

1. A pharmacologically active composition for improving lactation in a lactating mammal, containing an effective amount of a synergistic combination of fenugreek seed and additive comprising:
   (a) about 70-80% fibre-depleted fenugreek seed fraction, and
   (b) about 20-30% additive
   wherein said additive comprises:
      about 1-4% (w/w) apple cider vinegar:
      about 10-14% (w/w) fennel seed powder:
      about 1-4% Saw Palmetto berry powder:
      about 1-4.9% (w/w) kelp powder: and
      about 3-7% methylsulfonylmethane (w/w),
   wherein said additive acts synergistically with the fenugreek seed to improve lactation.

2. The composition of claim 1, wherein the fiber-depleted fenugreek seed fraction is produced from the cotyledon fraction of the fenugreek seed.

3. The composition of claim 1, wherein composition is pre-packaged in a single ration form and the single ration form comprises from about 0.1 lb to about 0.2 lb of the composition.

4. The composition of claim 1, wherein the composition is effective to improve lactation and milk production in a dairy animal, without causing an increase in somatic cell counts, as compared to somatic cell counts in an animal not fed the composition.

5. The composition of claim 1, wherein the composition is effective to improve lactation and milk production in a dairy animal, without causing a change in milk composition, as compared to milk composition in an animal not fed the composition.

* * * * *